United States Statutory Invention Registration [19]

Koppes et al.

[11] Reg. Number: H352

[43] Published: Oct. 6, 1987

[54] BIS(2-FLUORO-2,2-DINITROETHOXY) 2,2,3,3,4,4,4-HEPTAFLUOROBUTOXYMETHANE AND A METHOD OF PREPARATION

[75] Inventors: William M. Koppes, Adelphi; Horst G. Adolph, Silver Spring, both of Md.

[73] Assignee: The United States of America as represented by the Secretary of the Navy, Washington, D.C.

[21] Appl. No.: 46,345

[22] Filed: May 1, 1987

[51] Int. Cl.[4] ..... C07C 79/343; C07C 43/303; C06B 25/00; C06B 45/10

[52] U.S. Cl. ..... 568/590; 568/945; 149/19.3; 149/88

*Primary Examiner*—John F. Terapane
*Assistant Examiner*—J. E. Thomas
*Attorney, Agent, or Firm*—K. E. Walden; R. D. Johnson

[57] ABSTRACT

Bis(2-fluoro-2,2-dinitroethoxy) 2,2,3,3,4,4,4-heptafluorobutoxymethane, (HFBF), $CF_3CF_2CF_2CH_2OCH[OCH_2CF(NO_2)_2]_2$, is an energetic plasticizer with a melting point of −18° C. and thermal stability up to 150° C. HFBF is miscible with polyfluoro- and polynitropolymers and useful as a plasticizer in plastic-bonded explosives.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BIS(2-FLUORO-2,2-DINITROETHOXY) 2,2,3,3,4,4,4-HEPTAFLUOROBUTOXYMETHANE AND A METHOD OF PREPARATION

BACKGROUND OF THE INVENTION

This invention relates to plastic-bonded explosives and more particularly to energetic plasticizers for plastic-bonded explosives.

Examples of energetic plasticizers which are currently used in plastic-bonded explosives (PBXs) are bis(2-fluoro-2,2-dinitroethyl)formal (FEFO), butanetriol trinitrate (BTTN), and trimethylolethane trinitrate (TMETN). These compounds have various disadvantages which include limited thermal stability (BTTN, TMETN), high volatility (FEFO), toxicity (FEFO), and high melting point (FEFO). In addition, these energetic plasticizers are not miscible with fluoropolymers and can therefore not be used with these desirable new binder materials for PBXs.

It would be desirable to provide a new high energy, thermally stable plasticizer which is also miscible with polyfluoro- and polynitropolymers but with a lower melting point.

SUMMARY OF THE INVENTION

Accordingly, an object of this invention is to provide a new energetic plasticizer for plastic-bonded explosives.

Another object of this invention is to provide an energetic plasticizer having good thermal stability.

A further object of this invention is to provide an energetic plasticizer having a low melting point.

Still another object of this invention is to provide an energetic plasticizer that is miscible with fluoropolymers.

These and other objects of this invention are achieved by providing a new compound bis(2-fluoro-2,2-dinitroethoxy) 2,2,3,3,4,4,4-heptafluorobutoxymethane and a method of preparing it.

DETAILED DESCRIPTION OF THE PREFERRED EMBODIMENT

This invention provides bis(2-fluoro-2,2-dinitroethoxy) 2,2,3,3,4,4,4-heptafluorobutoxymethane (HFBF) which has been found to act as a general plasticizer for polyethylene glycol as well as various nitro-containing prepolymers, and also for highly fluorinated prepolymers such as the polyformal of 2,4,4,5,5,6,6-heptafluoro-2-trifluoromethyl-3-oxa-1,7-heptanediol, $HOCH_2CF_2CF_2OCF(CF_3)CH_2OH$. It is thermally stable up to 150° C. HFBF has a density of 1.68 g/cm$^3$ (22° C.) and its heat of formation is estimated to be −594 kcal/mol, and the calculated detonation pressure is 228.9 kbar. HFBF has a very low melting point (−18° to −19° C.) compared with other nitroplasticizers of similar energy content such as FEFO (+14° C.) or trifluoroethoxyFEFO (−1° to −3° C.). Its volatility is slightly lower than that of FEFO (0.0108 vs. 0.0167 mg/min at 117° C.). Thus HFBF exhibits a set of properties which is unmatched by any other energetic plasticizer of comparable energy content. In addition to being useful as a unitary plasticizer, HFBF may also be used in admixture with other plasticizers to further improve and/or modify specific properties such as energy content or melting point.

Bis(2-fluoro-2,2-dinitroethoxy) 2,2,3,3,4,4,4-heptafluorobutoxymethane, $CF_3CF_2CF_2CH_2OCH[OCH_2CF(NO_2)_2]_2$, is prepared from 2-fluoro-2,2-dinitroethanol, $CF(NO_2)_2CH_2OH$, and 2,2,3,3,4,4,4-heptafluoro-1-butanol, $CF_3CF_2CF_2CH_2OH$, by the following reaction sequence as illustrated in Examples 1, 2, and 3:

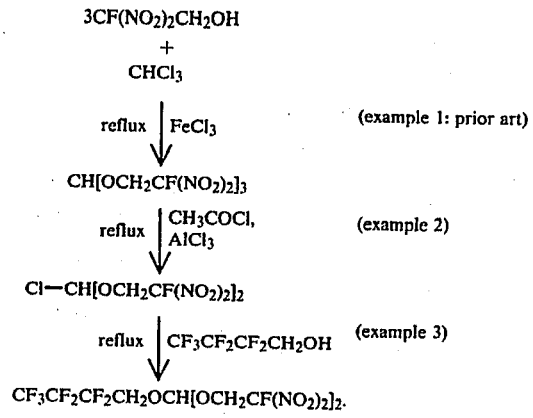

Tris(2-fluoro-2,2-dinitroethoxy)methane, $CH[OCH_2CF(NO_2)_2]_3$, is a prior art compound which is synthesized by reacting three moles of 2-fluoro-2,2-dinitroethanol with one mole of chloroform by refluxing the reactants in the presence of ferric chloride as a catalyst. The conditions of this reaction are illustrated by example 1 which is incorporated from U.S. Pat. No. 3,388,147, entitled "2-Fluoro-2,2-Dinitroethyl Carbonates and Production Thereof," which was issued on June 11, 1968, to Mortimer J. Kamlet et al. (see col. 3, example III).

Next the tris(2-fluoro-2,2-dinitroethoxy)methane is refluxed with aluminum chloride and acetyl chloride to produce chloro bis(2-fluoro-2,2-dinitroethoxy)methane as illustated by example 2.

Finally, one mole of 2,2,3,3,4,4,4-heptafluoro-1-butanol is reracted with each mole of chloro bis(2-fluoro-2,2-dinitroethoxy)methane to produce the desired product bis(2-fluoro-2,2-dinitroethoxy) 2,2,3,3,4,4,4-heptafluorobutoxy)methane under conditions illustrated by example 3. The choice of a solvent for this step is not critical. Any inert solvent in which the reactants are soluble and which has a suitable boiling point may be used. Suitable solvents include dichloromethane, 1,1-dichloroethane 1,2-dichloroethane, 1,1,2-trichloroethane, or mixtures thereof.

The general nature of the invention having been set forth, the following examples are presented as specific examples thereof. It will be understood that the invention is not limited to these specific examples but is susceptible to various modifications that will be recognized by one of ordinary skill in the art.

EXAMPLE 1

Prior Art

Tris(2-fluoro-2,2-dinitroethoxy)methane [i.e., tris(2-fluoro-2,2-dinitroethyl)orthoformate]

"A mixture of 0.5 g. anhydrous ferric chloride and 10 ml. chloroform was placed in a 30 ml. round-bottom flask fitted with a magnetic stirre and a reflux condenser connected through a bubbler to a methanol gas trap. 2-fluoro-2,2-dinitroethanol, 2.0 g. (0.013 mole) was added and the mixture stirred and refluxed for 24 hours, after which time the mixture was collected [sic] to room temperature and the solvent removed in vacuo.

"The residue was drowned in iced water, stirred until the ferric chloride dissolved and the crystalline product collected. Recrystallization of this material from chloroform-hexane gave 1.39 g. (68%) pure tris(2-fluoro-2,2-dinitroethyl)orthoformate (FDNEOF) as fine colorless needles, M.P. 110°-11.2°."

EXAMPLE 2

Chloro bis(2-fluoro-2,2-dinitroethoxy)methane

A solution of tris(2-fluoro-2,2-dinitroethoxy)methane (23.6 g, 0.050 mol), aluminum chloride (12.0 g, 0.090 mol) and acetyl chloride (200 g) was refluxed for 1.5 hours and then concentrated on a rotary evaporator to a viscous liquid. This was extracted with chloroform (2×50 ml). After treatment with activated charcoal (2 g.), this solution was filtered and concentrated (rot. evap., 40° C. bath) to 23 g. of residue from which 8.53 g. (87%) of 2-fluoro-2,2-dinitroethyl acetate (bp 40°−3° C./0.1 mm) was removed by distillation. The residual liquid (14.14 g, 80% yield) was chloro bis(2-fluoro-2,2-dinitroethoxy)methane, free of contaminants by $^1H$ NMR analysis. Anal. Calcd for $C_5H_5ClF_2N_4O_{10}$: C, 16.94; H 1.42; Cl, 10.00; F, 10.72; N, 15.80. Found: C, 17.10; H, 1.78; Cl, 10.08; F, 10.71; N, 15.42

EXAMPLE 3

Bis(2-fluoro-2,2-dinitroethoxy) 2,2,3,3,4,4,4-heptafluorobutoxymethane(HFBF)

A solution of 9.26 g (0.026 mol) of the chloro bis(2-fluoro-2,2-dinitroethoxy)methane (Example 2), 6.00 g (0.030 mol) of 2,2,3,3,4,4,4-heptafluoro-1-butanol, and 20 ml of 1,2-dichloroethane was refluxed for four hours. Volatiles were removed on a rotary evaporator (40° C. bath) and the residue absorbed on 6 g of silica gel (Silica Gel 60, 70-230 mesh). The product mixture was separated on a 100 g Silica Gel column with hexane/dichloromethane (4/1) to give 1.68 g. of bis(2,2,3,3,4,4,4-heptafluorobutoxy) 2-fluoro-2,2-dinitroethoxymethane and 11.57 g (86%) of bis(2-fluoro-2,2-dinitroethoxy) 2,2,3,3,4,4,4-heptafluorobutoxymethane, (HFBF), mp −19° C. to −18° C.; $^1H$ NMR ($CDCl_3$) δ5.67 (s, 1), 4.79 (d, 4, J=16 Hz), 4.16 (t, 2, J=14 Hz). Anal. Calcd for $C_9H_7F_9N_4O_{11}$: C, 20.86; H, 1.36; N, 10.81; F, 33.01. Found: C, 20.88; H, 1.32; N, 10.68; F, 32.81.

Obviously, numerous modifications and variations of the present invention are possible in light of the above teachings. It is therefore to be understood that within the scope of the appended claims the invention may be practiced otherwise than as specifically described herein.

What is claimed is:

1. Bis(2-fluoro-2,2,-dinitroethoxy) 2,2,3,3,4,4,4-heptafluorobutoxymethane, $CF_3CF_2CF_2CH_2OCH[OCH_2CF(NO)_2]_2$.

2. A method of preparing bis(2-fluoro-2,2-dinitroethoxy) 2,2,3,3,4,4,4-heptafluorobutoxymethane comprising the following steps in order:

(1) refluxing tris(2-fluoro-2,2-dinitroethoxy)methane with aluminum chloride and acetyl chloride to produce chloro bis(2-fluoro-2,2-dinitroethoxy)methane;

(2) reacting one mole of 2,2,3,3,4,4,4-heptafluoro-1-butanol with each mole of chloro bis(2-fluoro-2,2.-dinitroethoxy)methane to produce bis(2-fluoro-2,2-dinitroethoxy) 2,2,3,3,4,4,4-heptafluorobutoxymethane; and (3) isolating the product bis(2-fluoro-2,2-dinitroethoxy) 2,2,3,3,4,4,4-heptafluorobutoxymethane.

3. The process of claim 2 wherein the reaction in step (2) is run under reflux in a solvent selected from the group consisting of dichloromethane, 1,1-dichloroethane, 1,2-dichloroethane, 1,1,2-trichloroethane, and mixtures thereof.

* * * * *